United States Patent
Wyrobnik et al.

(10) Patent No.: US 9,446,101 B2
(45) Date of Patent: Sep. 20, 2016

(54) AGENT FOR USE IN THE CASE OF FRUCTOSE INTOLERANCE

(71) Applicant: PRO NATURA GESELLSCHAFT FUR GESUNDE ERNAHRUNG MBH, Frankfurt am Main (DE)

(72) Inventors: Daniel Henry Wyrobnik, Frankfurt am Main (DE); Isaac Harry Wyrobnik, Frankfurt am Main (DE); Elliad Ronen Silcoff, Tel Aviv (IL)

(73) Assignee: Pro Natura Gesellschaft fur gesunde Ernahrung mbH (DE)

( * ) Notice: Subject to any disclaimer, the term of this patent is extended or adjusted under 35 U.S.C. 154(b) by 0 days.

(21) Appl. No.: 13/674,841

(22) Filed: Nov. 12, 2012

(65) Prior Publication Data

US 2013/0224171 A1 Aug. 29, 2013

Related U.S. Application Data

(63) Continuation of application No. 12/093,822, filed as application No. PCT/IB2006/003223 on Nov. 15, 2006, now abandoned.

(60) Provisional application No. 60/757,414, filed on Jan. 10, 2006, provisional application No. 60/757,424, filed on Jan. 10, 2006, provisional application No. 60/831,050, filed on Jul. 17, 2006, provisional application No. 60/831,174, filed on Jul. 17, 2006.

(30) Foreign Application Priority Data

| Nov. 16, 2005 | (DE) | 10 2005 055 081 |
| Nov. 23, 2005 | (DE) | 10 2005 056 169 |
| Dec. 16, 2005 | (DE) | 10 2005 060 768 |
| Dec. 16, 2005 | (DE) | 10 2005 060 769 |
| Jan. 4, 2006 | (DE) | 10 2006 000 873 |
| Jan. 4, 2006 | (DE) | 10 2006 000 881 |
| Jan. 5, 2006 | (DE) | 10 2006 001 015 |
| Mar. 15, 2006 | (DE) | 10 2006 012 244 |
| Mar. 22, 2006 | (DE) | 10 2006 013 624 |
| Mar. 27, 2006 | (DE) | 10 2006 014 423 |

(51) Int. Cl.
*A61K 38/44* (2006.01)
*A61K 38/47* (2006.01)
*A61K 9/48* (2006.01)
*A61K 38/52* (2006.01)
*C12Q 1/32* (2006.01)

(52) U.S. Cl.
CPC ............. *A61K 38/47* (2013.01); *A23L 5/20* (2016.08); *A23L 29/06* (2016.08); *A61K 9/48* (2013.01); *A61K 38/443* (2013.01); *A61K 38/52* (2013.01); *C12Q 1/32* (2013.01); *C12Y 101/01124* (2013.01); *C12Y 302/0102* (2013.01); *C12Y 302/01026* (2013.01); *C12Y 503/01005* (2013.01); *A23V 2002/00* (2013.01); *G01N 2333/904* (2013.01); *G01N 2800/04* (2013.01); *G01N 2800/38* (2013.01)

(58) Field of Classification Search
CPC ...... A61K 9/20; A61K 38/44; A61K 38/443; A61K 38/47
See application file for complete search history.

(56) References Cited

U.S. PATENT DOCUMENTS

| 4,699,882 A * | 10/1987 | Visuri | 435/188 |
| 5,650,156 A * | 7/1997 | Grinstaff et al. | 424/400 |
| 5,759,539 A * | 6/1998 | Whitmire | 424/94.3 |
| 6,165,500 A * | 12/2000 | Cevc | 424/450 |
| 6,306,445 B1 * | 10/2001 | Xu et al. | 426/20 |
| 6,395,299 B1 * | 5/2002 | Babich et al. | 424/484 |
| 2008/0044504 A1 * | 2/2008 | Komaki et al. | 424/769 |
| 2008/0096260 A1 * | 4/2008 | Budolfsen et al. | 435/135 |

FOREIGN PATENT DOCUMENTS

| JP | 63230085 A * | 9/1988 | C12N 9/96 |
| WO | WO 2005/055934 | * 6/2005 | |

OTHER PUBLICATIONS

Asano et al., JP 63230085. 1988, translation pp. 1-13.*
Fukagawa, Naomi K., "Deficiency of Intestinal Maltase and Invertase", Nutrition Reviews, 1962, vol. 20, No. 1, pp. 15-17.*

* cited by examiner

*Primary Examiner* — Laura Schuberg
(74) *Attorney, Agent, or Firm* — Daniel Feigelson; Fourth Dimension LP

(57) ABSTRACT

5-D-fructose dehydrogenase, optionally in combination with invertase and/or maltase and/or glucose isomerase, may be used to treat fructose intolerance. Other embodiments are also disclosed.

16 Claims, No Drawings

AGENT FOR USE IN THE CASE OF FRUCTOSE INTOLERANCE

This is a continuation of U.S. Ser. No. 12/093,822, which is a §371 application of PCT/IB2006/003223, filed Nov. 15, 2006, and claims the benefit under 35 U.S.C. §120 of said PCT application, and further claims the benefit under 35 U.S.C. §119(e) of U.S. Provisional Patent Application Ser. No. 60/757,414, filed Jan. 10, 2006, U.S. Ser. No. 60/757,424 filed Jan. 10, 2006, U.S. Ser. No. 60/831,050, filed on Jul. 17, 2006, and U.S. Ser. No. 60/831,174, filed on Jul. 17, 2006. This application claims the benefit and/or priority of all these applications, as appropriate, and the contents of these applications are incorporated herein by reference.

The present invention refers to an agent for use in the case of fructose intolerance. In the sense of this patent application, fructose intolerance does not only mean the medically defined fructose intolerance and disorders of fructose metabolism (further details below), but any form of impairment and affliction of health and well being which is caused by the administration of fructose or fructose containing foodstuffs or by the release of fructose in the digestive tract of humans or animals from other substances, such as e.g. sucrose.

In the context of this patent application, the terms food and foodstuff are used as synonyms. They mean to also include feed in the sense of animal feed. The term "special foodstuff" is defined later on and has a particular meaning according to the invention.

Fructose is a ketohexose and an important ingredient of food providing energy. It is present as a component of many di- and oligosaccharides, but also as free fructose, or as both in numerous foodstuffs. Fructose is contained in food, such as fruits and fruit juices in high amounts, but in particular also in sucrose which is cleaved to fructose and glucose in the organism. In the following, 'fructose containing' should mean all substances and foodstuffs which either contain fructose in pure form or from which fructose can be released in the digestive tract.

In contrast to glucose, fructose is assimilated into the mucosa cells of the small intestine by eased carrier-mediated diffusion. The enzymatic degradation starts in the liver by the action of the adenosine triphosphate (ATP) dependent fructokinase, wherein fructose is reacted to fructose 1-phosphate. In the liver and in the kidneys, fructose 1-phosphate is cleaved to glycerine aldehyde and dihydroxyacetone phosphate by aldolase B.

Three different disorders of fructose metabolism are known, namely the hereditary fructose intolerance, the intestinal fructose intolerance and the lack of fructose 1,6-diphosphatase. In addition, fructosuria is known, which does not need to be treated according to present knowledge.

Hereditary fructose intolerance (HFI) is caused by a lack of aldolase B, an enzyme which is present in the intestinal mucosa, in the liver, in lymphocytes and in the kidneys. Normally, this enzyme degrades over intermediate steps fructose 1-phosphate to fructose 1,6-biphosphate. In the case of lack of aldolase B, an accumulation of fructose 1-phosphate results, and due to inhibition of the degradation of glycogen and the gluconeogenesis severe hypoglycaemias appear, associated with break-out of sweat, tremor, vomiting and cramps after fructose intake. In an unknown manner, acidosis, kidney injuries and aminoaciduria may occur. In babyhood, there is the danger of haemorrhages up to cot death.

Intestinal fructose intolerance exhibits other symptoms. It is wide-spread and occurrs with increasing frequency, in particular in the western industrialized nations. Intestinal fructose intolerance is caused by a disorder of the resorption of fructose as a result of the impairment of transport processes in the mucosa of the small intestine. The sufferer shows unclear abdominal distress/symptoms and as a result of the bacterial degradation of the carbohydrates which have been transferred into the colon increased intestinal production of gas. The affliction comprises e.g. bloated feeling, flatulences, colic-like bellyaches, aqueous diarrhoeas and noises in the bowels. Often, a wrong diagnosis of irritable colon is made.

Lack of fructose 1,6-diphosphatase is a defiency of this key enzyme in the gluconeogenesis pathway. This deficiency causes an increase of the level of lactate in the blood after ingestion of fructose, and hypoglycaemias in the case of an empty stomach with lactacidosis, cramps of muscular hypotonia and coma. Through an adiposis of the liver, also hepatomegalia may occur.

Not each disorder of fructose metabolism necessarily results in severe fructose intolerance. However, even in the case of mild disorders of fructose metabolism, impairments of health or well being can often be observed, which until now could only be influenced by a modification of the diet. Also, an excessive intake of fructose-containing food may result in impairments of health.

Until now, the symptoms and impairments mentioned above could only be avoided by adhering to a fructose-, sucrose- and sorbitol-free diet. However, maintaining such a diet is very difficult for the sufferers, since fructose is contained in all fruits and many vegetables and is used extensively in the food industry as a sweetener. Also all foodstuffs which contain e.g. sucrose (household sugar) have to be avoided. It is not only difficult to stick to a corresponding diet—in the case of hereditary fructose intolerance even a very strict diet—it is also extremely unfavourable in respect to the nutrition physiology and significantly impairs the quality of life of the sufferers. The sufferers and the persons skilled in the art (for example physicians, medical specialists, nutrition scientists, nutrition consultants, special journalists, etc.) have assumed for decades that there is no alternative to sticking to a diet. Research aimed at finding an alternative to keeping a diet has not been successful. An agent that would make it possible to avoid keeping a diet, allowing the intake of fructose containing food, would thus meet the urgent need of many sufferers which has existed for decades. A strong prejudice in the art and by the sufferers would be overcome, leading to a dramatic improvement of the possibilities for the therapy and nutrition in the case of fructose intolerance, since there is, except for the diet, simply no therapy available. Such an agent would also stop the hitherto unsuccessful efforts of persons skilled in the art to enable the sufferers to enjoy a normal diet, including fructose-containing meals, without affliction. The importance of such an agent becomes evident if one considers the most severe and dangerous consequences for the health of the sufferers with hereditary fructose intolerance in case they e.g. ingest fructose unknowingly, inadvertently or unintentionally. This would be even more valid for an agent which in addition has no negative side effects for the health.

Thus, there is provided in accordance with embodiments of the present invention an effective agent for use in the case of mild impairments of the fructose metabolism as well as in the cases of hereditary and intestinal fructose intolerance and the lack of fructose 1,6-diphosphatase, especially in order to allow the intake of fructose containing foodstuffs even in the case of fructose intolerance. Further, there is provided in accordance with embodiments of the invention an agent to enable the sufferers of fructose intolerance to eat foods which they had to avoid until now due to their fructose content. Furthermore, in accordance with some embodiments of the invention an agent is to be provided which can reduce or eliminate the occurrence of symptoms of fructose intolerance after the intake of fructose.

The subject matter of the invention is an agent which comprises 5-D-fructose dehydrogenase (syn. fructose 5-dehydrogenase). The agent according to the present invention may facilitate the conversion of fructose in the food into 5-keto-D-fructose via dehydrogenation. Thus it is changed in such a manner that it is not available for the bacterial metabolism, which is characterized by fermentation in the intestine, nor can an accumulation of fructose 1-phosphate in the liver or elsewhere take place. Thus, an increase of the level of lactate in the blood can be avoided, too. The invention thus provides compositions and methods that can be used to enable sufferers of fructose intolerance to ingest fructose-containing foods.

A further subject matter of the present invention is an agent which reduces the bioavailability of fructose in the human or animal body with the help of 5-D-fructose dehydrogenase.

Still further, a subject matter of the invention is an agent for use in the case of impaired fructose metabolism, including fructose intolerance, which contains a compound effecting the dehydrogenation of fructose to 5-keto-D-fructose. This conversion may be achieved e.g. enzymatically by a 5-D-fructose dehydrogenase.

Preferably, the agent according to the invention comprises a 5-D-fructose dehydrogenase.

Hence, a subject matter of the invention is in particular an agent for use in the case of fructose intolerance which comprises a 5-D-fructose dehydrogenase.

Another subject matter of the invention is the use of 5-D-fructose dehydrogenase in the case of a impaired fructose metabolism, including fructose intolerance.

According to the present invention, a 5-D-fructose dehydrogenase can also be used for lowering the content of fructose in a foodstuff.

In the context of this application a 5-D-fructose dehydrogenase is an enzyme which can catalyse the dehydrogenation of fructose to 5-keto-D-fructose. A possible production method for a 5-D-fructose dehydrogenase is for example described in Ameyama et al., Journal of Bacteriology 1981, 814-823, "D-Fructose Dehydrogenase of *Gluconobacter industrius*: Purification, Characterization and Application of Enzymatic Microdetermination of D-Fructose", the content of which is incorporated herein by reference.

In the context of this application special foodstuffs are foodstuffs for particular nutritional uses, foods for special medical purposes, food supplements, dietary supplements, dietetic food supplements, health foods, nutraceuticals and food additives. In the context of this application the term foodstuff means to include special foodstuffs as used herein, where applicable.

The invention permits the easy conversion of fructose in a foodstuff into a form that can avoid the problems associated with fructose intolerance. Thus, the invention also enables the sufferers of fructose intolerance to eat foodstuffs which they had to avoid until now due to the fructose content of these foodstuffs.

According to the present invention, 5-D-fructose dehydrogenase is further disclosed for use in medicine, for example as a pharmaceutical composition. Accordingly, the subject matter of the invention includes a product which may be 5-D-fructose dehydrogenase or may comprise this enzyme for the use in a medical treatment. In particular, a method for the therapeutic treatment of the human or animal body is addressed. In the context of this invention, a pharmaceutical composition is a product, in particular a substance or substance mixture, suited for use in surgical or therapeutic treatment of the human or animal body and for diagnostic methods which are performed on the human or animal body. In the context of this application pharmaceutical compositions therefore mean to include for example products, in particular substances or substance mixtures, which are meant or suitable for curing, alleviating, preventing or detecting fructose intolerance.

The term "treating" when used in connection with the foregoing disorders includes amelioration, prevention or relief from the symptoms and/or effects associated with these disorders and includes the prophylactic administration of an enzyme or a mixture thereof to diminish the likelihood or seriousness of the condition.

According to a further aspect, the present invention provides a foodstuff which comprises 5-D-fructose dehydrogenase. Still further, the present invention provides a foodstuff which contains a sufficient amount of 5-D-fructose dehydrogenase for converting fructose into 5-keto-D-fructose. Such a foodstuff may advantageously be produced for example by a process for treating a foodstuff where the foodstuff is brought into contact with 5-D-fructose dehydrogenase under such conditions, that the enzyme is able to convert fructose into 5-keto-D-fructose. Such a foodstuff has a reduced fructose content compared to the untreated foodstuff and is therefore for the first time suitable for consumption in the case of fructose intolerance. A foodstuff can be produced for example by a method where a 5-D-fructose dehydrogenase is added to the foodstuff in such a way that the dehydrogenating effect of the 5-D-fructose dehydrogenase starts only after the intake of the foodstuff. Such a foodstuff containing 5-D-fructose dehydrogenase has the same taste as an untreated foodstuff. Therefore, for the first time such foodstuffs are suitable for consumption in the case of fructose intolerance due to the reduction of the fructose content which takes place after the intake.

According to a further aspect of the present invention a medical device is provided which comprises 5-D-fructose dehydrogenase. Still further, a medical device is provided which comprises 5-D-fructose dehydrogenase in an amount being effective for the conversion of fructose into 5-keto-D-fructose.

The invention will now be described with respect to different aspects thereof in more detail. Regarding the meaning of the term "agent", in the following this is to be understood to include a foodstuff, a special foodstuff, a medical device or a pharmaceutical composition.

5-D-Fructose dehydrogenase is a substance which has been known for nearly 40 years without being used for anything but analytical purposes. Accordingly, it was never used in the medical/pharmaceutical field, particularly not for the therapeutic treatment of the human or animal body or for diagnostic purposes at the human or animal body and very particularly not in the case of disorders of the fructose metabolism in humans or animals. Thus, the present invention addresses the first medical indication for 5-D-fructose dehydrogenase.

The agent according to the present invention may be taken orally prior to meals, preferably immediately before meals, together with a meal or immediately after the meal so that it can exert its dehydrogenating effect on fructose in the food pulp. The agent may contain the enzyme without further additives. However, it is preferable that the agent according to the present invention further contains additives which are, for example, pharmaceutically acceptable ingredients and/or ingredients acceptable for foodstuffs, such as for example extenders, binders, stabilisers, preservatives, flavourings etc. Such additives are conventional and well known for the production of pharmaceutical compositions, medical devices, foodstuffs, and special foodstuffs, and the person skilled in the art knows which additives in which amounts are suitable for certain dosage forms. Particularly preferably, The agent according to the present invention may contain additives, such as dicalcium phosphate, lactose, modified starch, microcrystalline cellulose, maltodextrin and/or fibersol.

It may be advantageous to add to the agent according to the invention an electron acceptor, for example in an amount of from 1:1 to 1:1000 (proportion of acceptor: substrate), preferably 1:2 to 1:200, more preferred in an amount of from 1:10 to 1:50. Examples of suitable acceptors are, but not limited to, $NAD^+$, $NADP^+$, $FAD^+$, vitamins, such as for example vitamin C, E or A, ferricyanide, ketones, aldehydes, 2,6-di-chloro-phenolindophenol, phenazine methsulfate, nitroblue tetrazolium and mixtures of such acceptors.

The agent according to the present invention can also be added to a foodstuff prior to ingestion. It can even be added to the foodstuff at the production stage with the purpose of developing its effect after ingestion of the foodstuff. This may be achieved, for example, by microencapsulation. With this, the useable fructose content of the foodstuff may be reduced without altering the taste of the foodstuff in a unfavourable manner. Hence, agents according to the present invention may comprise 5-D-fructose dehydrogenase that will be released, or become effective by other means, only in the digestive tract of a human or animal, in particular in the stomach or the small intestine. Therefore, the invention can be used, for example, in the production of sweets, fruit preparations (e.g. apple puree), jam, honey, chocolate and chocolate products, baked products (e.g. biscuits and cakes), breads, pastas, vegetable dishes, potato dishes, ice cream, cereals, dairy products (e.g. fruit yoghurt and pudding), fructose containing beverages, fructose containing sauces (e.g. tomato ketchup) and fructose containing sweeteners. For dishes which are cooked or baked, the agent according to the present invention could e.g. be mixed into or sprinkled onto it after cooling down.

Since fructose is used as a sweetener in high amounts in foodstuffs for diabetics, it is beneficial to add the agent according to the present invention to such food before eating or already at the production stage. This allows fructose intolerant diabetics the intake of food for diabetics, such as the above mentioned foodstuffs in a form suitable for diabetics (diabetes food).

The agent according to the present invention may also be added to a foodstuff in order to exert its effect on fructose originating from another foodstuff after ingestion. The agent can for example be added to a spread so that the reduction of the fructose contained in the bread occurs after eating the bread with the spread on it without impairing the taste of the bread. Another example would be spice mixes.

The agent according to the present invention may also be used in immobilised form. This is particularly useful for the treatment of liquid foodstuffs. For example, the 5-D-fructose dehydrogenase may be embedded in a matrix which is permeable for fructose: When a fructose containing liquid foodstuff flows past the enzyme containing matrix, then fructose is extracted from the foodstuff by the action of the enzyme and converted to 5-keto-D-fructose.

Subject of the present invention are also agents which contain 5-D-fructose dehydrogenase in addition to other active ingredients.

The agent may be formulated in any form which is suitable for the intended route of administration. A preferred route of administration is oral administration. For oral administration, the agent may be formulated for example in the form of capsules (coated or non-coated) containing powder, coated or non-coated pellets, granules or micro-/mini-tablets or in the form of tablets (coated or non-coated) pressed from powder, coated or non-coated pellets, dragees or micro-/mini-tablets. The agent may also be formulated for example in the form of gel caps or in liquid form as solution, drops, suspension or gel. The agent may also be formulated e.g. as dried or wet moist oral supplement. The formulation of the agent according to the present invention as powder is particularly suitable for admixing with foodstuff. The powder may be sprinkled onto a meal or mixed into a pulp or beverage. It is particularly beneficial, if the agent offered as bulk powder is packaged in single dosage amounts, such as in single bags or capsules, or if it is provided in a dosing dispenser.

For oral administration, 5-D-fructose dehydrogenase may be contained used with acceptable excipients and/or carriers. The term "acceptable carrier" refers to a carrier for pharmaceutical use, that delivers the active ingredient to its target site of activity without causing significant harm to the treated human or animal. However, the exact form of the carrier is not of substantial importance.

The total content of the carrier within an agent containing 5-D-fructose dehydrogenase is preferably between 5 and 99.9% by weight of the composition, more preferably between 10 and 80% even more preferably between 25 and 60%.

Suitable excipients and/or carriers include but are not limited to maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethyl cellulose, corn starch, modified starch, fibersol, gelatine, hydroxypropylmethyl cellulose and the like (including mixtures thereof).

Preferable carriers include calcium carbonate, magnesium stearate, maltodextrin, dicalcium phosphate, modified starch, microcrystalline cellulose, fibersol, gelatine, hydroxypropylmethyl cellulose and mixtures thereof.

The different ingredients and the excipient and/or carrier may be mixed and formed into the desired form using common methods well known to the skilled person. The administration form according to the present invention which is suited for the oral route, such as e.g. tablet or capsule, may be coated with a coating which is resistant against low pH values (approximately pH 1 to 2.5) and which dissolves at a pH value of approximately 3.0 to 8.0, preferably at a pH value of 3.0 to 6.5 and particularly preferable at a pH value of 4.0 to 6.0. An optionally used coating should be in accordance with the pH optimum of the enzyme used and its stability at pH values to which the formulation will be exposed. Also a coating may be used which is not resistant to low pH values but which delays the release of the enzyme at low pH values. It is also possible to prepare the agent according to the present invention as coated (see above) pellets, granules or micro-/mini-tablets which can be filled into coated or non-coated capsules or which can be pressed into coated or non-coated tablets. Suitable coatings are, for example, cellulose acetate phthalate, cellulose derivates, shellac, polyvinylpyrrolidone derivates, acrylic acid, polyacrylic acid derivates and polymethyl methacrylate (PMMA), such as e.g. Eudragit® (from Röhm GmbH, Darmstadt, Germany), in particular Eudragit® L30D-55. The coating Eudragit® L30D-55 is dissolved, for example, at a pH value of 5.5 and higher. If it is desired to release the enzyme already at a lower pH value, this may be achieved e.g. by the addition of sodium hydroxide solution to the coating agent Eudragit® L30D-55, because in this case carboxyl groups of the methacrylate would be neutralised. Therefore, this coating will be dissolved, for example, already at a pH value of 4.0 provided that 5% of the carboxyl groups are neutralised. The addition of about 100 g of 4% sodium hydroxide solution to 1 kg of Eudragit® L30D-55 would result in a neutralisation of about 6% of the carboxyl groups. Further details about formulation methods and administration methods can be found in the 21$^{st}$ edition of "Remington: The Science & Practice of Pharmacy", published 2005 by Lippincott, Williams & Wilkins, Baltimore, USA, in the Encyclopedia of Pharmaceutical Technology (Editor James Swarbrick) and in Prof. Bauer "Lehrbuch der Pharmazeutischen Technologie", 18$^{th}$ edition, published 2006 by Wissenschaftliche Verlagsgesellschaft (ISBN 3804-72222-9). The contents of these documents are incorporated herein by reference.

Other suitable pharmaceutically acceptable carriers for use in the present invention include, but are not restricted to water, mineral oil, ethylene glycol, propylene glycol, lanolin, glyceryl stearate, sorbitan stearate, isopropyl myristate, isopropyl palmitate, acetone, glycerine, phosphatidylcholine, sodium cholate or ethanol.

The compositions for use in the present invention may also comprise at least one co-emulsifying agent which includes but is not limited to oxyethylenated sorbitan monostearate, fatty alcohols, such as stearyl alcohol or cetyl alcohol, or esters of fatty acids and polyols, such as glyceryl stearate.

The agents to be used according to the present invention may be provided in a stabilized form. Generally, stabilisation methods and procedures which can be used include any and all methods for the stabilisation of chemical or biological material which are known in the art and suited for the particular purpose, comprising e.g. the addition of chemical agents, methods which are based on temperature modulation, methods which are based on irradiation or combinations thereof. Chemical agents that may be used according to the present invention include, among others, preservatives, acids, bases, salts, antioxidants, viscosity enhancers, emulsifying agents, gelatinizers, and mixtures thereof.

Usually, the industrial production of enzymes is performed in a technical fermentation process using suitable microorganisms (bacteria, moulds, fungi). Usually, the strains are recovered from natural ecosystems according to a special screening protocol, isolated as pure cultures as well as improved in their properties with respect to the enzyme spectrum and biosynthesis performance (volume/time yield). Enzyme production may also be carried out by methods developed in the future.

The 5-D-fructose dehydrogenase is commercially available (e.g. Sigma-Aldrich and Toyobo Enzymes) and is usually prepared in a microbiological way with the help of the microorganism *Gluconobacter industrius*. However, the invention is not limited to the enzymes which are presently commercially available, but relates generally to enzymes which can catalyse the conversion of fructose—specifically or non specifically—to 5-keto-D-fructose. A person skilled in the art can prepare suitable further enzymes by methods presently known in the art or by methods which may be developed in the future, for example by mutagenesis of the gene for 5-D-fructose dehydrogenase which is present in *Gluconobacter industrius*. The enzyme may also be prepared with the help of other microorganisms, such as fungi, in sufficient amounts and the required purities, also by the use of the genetic engineering methods which are presently known or may be developed in the future. For example, if it is desired to produce the enzyme with another microorganism, then the genetic information of a microorganism which has been found initially by extensive screening and which has proved to be a suitable source of the enzyme with the desired properties can be transferred to a microorganism which is normally used for the production of enzymes. Also, the modification of the enzyme itself and the production of the enzyme by means of methods which are presently known or may be developed in the future in the area of industrial enzyme development and enzyme production, such as genetic engineering, is possible. The use and the manner of performing of all these methods for developing and producing the enzyme with the desired purities and activities and with the desired properties, in particular with respect to stabilities of the enzyme regarding the pH value, regarding optima of the pH value, temperature stabilities and temperature optima, are well known to a person skilled in the art. The explanations in chapter 2 (page 82 to page 130) of the textbook "Lebensmittel-Biotechnologie and Ernährung" of Heinz Ruttloff, Jürgen Proll and Andreas Leuchtenberger, published by Springer Verlag 1997 (ISBN 3-540-61135-5) describe these methods in detail. Further information can be found These methods are also described in "Advances in Fungal Biotechnology for Industry, Agriculture, and Medicine" by Jan S. Tkacz, Lene Langeand (published in 2004, ISBN 0-306-47866-8), in "Enzymes in Industry: Production and Applications" by Wolfgang Aehle (Editor), published in 2004, ISBN 3527295925 and in "Microbial Enzymes and Biotransformations" by Jose-Luis Barredo (Humana Press 2005, ISBN 1588292533). These documents are herewith incorporated into the patent application by reference. All this also applies to the enzymes mentioned below that can optionally be added to the agent according to the present invention.

The activity of 5-D-fructose dehydrogenase is defined in units (assay available e.g. from Sigma-Aldrich), wherein one unit is the amount of 5-D-fructose dehydrogenase that converts one micromole of D-fructose to 5-keto-D-fructose per minute at pH 4.5 and 37° C. The assay is available from Sigma-Aldrich. Generally, the activity of the 5-D-fructose dehydrogenase per dose unit should be between 10 and 5 million units, preferably between 25 and 2.5 million units and particularly preferably between 50 and 1 million units. The wide range of the above mentioned dosages may be explained by the fact that the agent according to the present invention is applicable to three different types of fructose intolerance, namely the hereditary fructose intolerance, the intestinal fructose intolerance and the lack of fructose 1,6-diphosphatase, each in different degrees of severity, as well as to mild disorders of the fructose metabolism. Furthermore, the different dosages also result from the fact that depending on the specific food intake widely varying amounts of fructose enter the organism.

The agent according to the present invention may comprise one or more additional enzymes, such as invertase (synonymous to beta-fructofuranosidase or betafructosidase). Invertase can cleave fructose off chemical compounds from the fructose side and may thus release fructose from such compounds. It can for example cleave sucrose (household sugar) to glucose and fructose. In another embodiment the agent according to the present invention also comprises the enzyme maltase (syn. alpha-glucosidase) alone or in combination with invertase. This enzyme may also release fructose by cleaving glucose from e.g. sucrose. By the addition of invertase and/or maltase to the agent according to the present invention, the endogenis release of fructose from fructose containing substances or foodstuffs, in particular from sucrose, may be both, promoted and accelerated, so that the conversion of fructose to 5-keto-D-fructose which is catalysed by the 5-D-fructose dehydrogenase may occur earlier. Therefore, the addition of invertase and/or maltase to the agent according to the present invention, may have the benefit of reducing the required amount of 5-D-fructose dehydrogenase. Such combinations have also never been used in the therapeutic treatment of the human or animal body or for diagnostic purposes of the human or animal body.

In another embodiment the agent according to the present invention also comprises the enzyme glucose isomerase. A glucose isomerase in the context of this application is an enzyme that is able to catalyze a conversion of fructose to glucose. This conversion can also be brought about, for example, by a xylose isomerase. Thus, such a xylose isomerase is, in the sense of this invention, also a glucose isomerase. A possible method for the production of a xylose isomerase is, for example, described in Yamanaka, Biochimica et Biophysika Acta, Volume 151 (3), 1968, 670-680, "Purification, Crystallization and Properties of the D-Xylose Isomerase from *Lactobacillus brevis*" and in Yamanaka, Methods in Enzymology, Volume 41, 1971, 466-471, "D-Xylose Isomerase from *Lactobacillus brevis*".

Glucose isomerase has the property of converting glucose into fructose and vice versa with an equilibrium concentration of approximately 50% glucose and 50% fructose. Glucose isomerase is therefore ideally suited for supporting the action of 5-D-fructose dehydrogenase: Fructose is a monosaccharide which is only slowly absorbed from the intestine into the bloodstream. In contrast Glucose is a monosaccharide which is absorbed quickly from the intestine into the blood stream and which does not pose a problem for people with fructose intolerance. If a fructose intolerant person ingest e.g. apple juice the glucose isomerase will try to establish the aforementioned equilibrium. Therefore the glucose isomerase will start to convert fructose into glucose. The glucose that results from this conversion process will be absorbed in the intestine. This prevents the achievement of the aforementioned equilibrium. Therefore the glucose isomerase will continue converting fructose to glucose in the food pulp until the aforementioned equilibrium is reached or until there in no fructose left. Thus, it can be beneficial to combine 5-D-fructose dehydrogenase not only with invertase and/or maltase but also with glucose isomerase. In this embodiment, as 5-D-fructose dehydrogenase converts fructose to 5-keto-D-fructose, at the same time the glucose isomerase converts fructose to glucose, which is also harmless for people with fructose intolerance.

Therefore, the addition of glucose isomerase to the agent according to the present invention, can reduce the required amount of 5-D-fructose dehydrogenase. The combination of 5-D-fructose dehydrogenase with glucose isomerase and optionally with invertase and/or maltase has also never been used in the therapeutic treatment of the human or animal body or for diagnostic purposes of the human or animal body.

Invertase and maltase are compounds which have been known for decades and are commercially available (e.g. BioCat Inc., Troy, USA, Novozymes A/S, Denmark, Sigma Aldrich or Toyobo Enzymes, Japan). So far, invertase has been used almost exclusively in the production of invert sugar, invert honey and chocolate dishes, such as e.g. chocolate candies. It has never been used before in combination with 5-D-fructose dehydrogenase in the medical/pharmaceutical field, and in particular not in the case of disorders of the fructose metabolism in humans or animals. Until now, this enzyme combination has never been used in the therapeutic treatment of the human or animal body or for diagnosis purposes. Thus, herewith the first medical indication for the combination of 5-D-fructose dehydrogenase and invertase is disclosed. The same applies to the combination of 5-D-fructose dehydrogenase with maltase and to the combination of 5-D-fructose dehydrogenase with invertase and maltase.

The activity of invertase is measured in Sumner Units (SU, assay available e.g. from Bio-Cat Inc., Troy, Va., USA). One SU is defined as the amount of the enzyme which converts 1 mg of sucrose to glucose and fructose under standard test conditions within 5 minutes at 20° C. and a pH value of 4.5. If the agent according to the present invention also contains invertase, the activity of the invertase per dose unit should be between 50 and 250,000 SU, preferably between 100 and 150,000 SU and particularly preferably between 150 and 100,000 SU per dose unit.

The activity of maltase is defined in units, wherein one unit is the amount of maltase which will convert maltose to D-glucose at a rate of one milligram per minute at 37° C. and a pH of 4.0 in a 10% maltose solution by weight.

Where the agent according to the present invention also contains maltase the activity per dose unit should be between 100 and 100,000 units, preferably between 200 and 50,000 units and particularly preferably between 500 and 20,000 units.

Glucose isomerase is a compound that has been known for more than 40 years and has only been used for starch saccharification to date. In the industry, it is commonly used in immobilized form for the conversion of glucose into fructose as well as for the conversion of fructose into glucose.

Glucose isomerase is commercially available (e.g. Sigma-Aldrich or Novozymes A/S, Denmark) and usually prepared in a microbiological way with the help of the microorganism *Streptomyces murinus*, Where the agent according to the present invention also contains glucose isomerase, the composition should contain glucose isomerase in an amount of 0.01 to 100,000 GIU, preferably of 0.05 to 10,000 GIU and particularly preferably of 0.1 to 1,000 GIU per dose unit. One unit of this enzyme is defined as a glucose isomerase unit (GIU) that converts 1 g of glucose into fructose at a pH value of 6.0 and at a temperature of 37° C. from a solution of initially 10% (percent by weight, i.e. 10 g of glucose +90 g of water) in 5 minutes.

If the agent according to the present invention comprises one or more of the aforementioned optional enzymes, then they should be used in sufficient amounts—as is the case for the 5-D-fructose dehydrogenase—so that they can develop a sufficient enzyme activity for the intended purpose, e.g. sufficient invertase, so that an amount of sucrose usually ingested with a normal meal (e.g. 15 g) can be cleaved.

The physiologically present electrolytes will generally be sufficient for the function of glucose isomerase.

But it may also be advantageous to add electrolytes to the agent according to the present invention, preferably in an amount of 0.0001% to 0.1% of the substrate (glucose). Examples of the electrolytes include, but are not limited to, MgSO$_4$, Na$_2$CO$_3$, NaHCO$_3$, NaOH, Na$_2$SO$_4$, MgCO$_3$, H$_2$SO$_4$, NaS$_2$O$_3$, NaS$_2$O$_5$ (including mixtures thereof).

It may also be advantageous to add metal ions, in particular cations, such as Mn$^{2+}$, Mg$^{2+}$, Ca$^{2+}$, Zn$^{2+}$, Fe$^{2+}$, Co$^{2+}$ or Cu$^{2+}$, including mixtures thereof, to the agent according to the present invention, namely preferably in a molar ratio of 10$^{-6}$ to 10$^{-2}$. For the above mentioned (xylose) glucose isomerase which is described by Yamanaka, in particular Mn$^{2+}$ is a suitable cation.

In the case of intestinal fructose intolerance it is particularly preferable that the agent according to the present invention may contain—besides 5-D-fructose dehydrogenase and optionally invertase and/or maltase and/or glucose isomerase—also glucose in an amount of 50 mg to 50,000 mg, preferably 500 mg to 25,000 mg and most preferably 1,000 mg to 15,000 mg per dose unit. This is because glucose accelerates the resorption of fructose in the intestine.

In the case of hereditary fructose intolerance it is particularly preferable that the agent according to the present invention may contain—besides 5-D-fructose dehydrogenase and optionally invertase and/or maltase and/or glucose isomerase—also folic acid in an amount of 1 mg to 100 mg, preferably 2 mg to 50 mg and particularly preferably 3 mg to 10 mg per dose unit. This is because folic acid increases the activity of aldolase B.

In case the agent according to the present invention is added to a foodstuff before ingestion or already at the production stage, the activity of 5-D-fructose dehydrogenase should be between 10 and 150,000 units, preferably between 25 and 100,000 units and particularly preferably between 50 and 50,000 units per gram fructose in the foodstuff.

Further, the present invention provides methods for diagnosing fructose intolerance, for example by administering to a person exhibiting the symptoms of fructose intolerance a capsule or other formulation comprising 5-D-fructose dehydrogenase or another suitable enzyme that converts fructose to a form that is biologically inactive in humans, or by administering to a person known to exhibit the symptoms of fructose intolerance both an amount of fructose and a capsule or other formulation comprising a sufficient amount of 5-D-fructose dehydrogenase or another suitable enzyme that converts fructose to a form that is biologically inactive in humans to convert at least a portion of the administered fructose to a form that is at least one of (a) biologically inactive in the human body, (b) not digestible in the human digestive tract and (c) not metabolizable in the human body, and assessing the results of the administration of the enzyme. In some embodiments, the portion is at least 50% of the administered fructose. In other embodiments, the portion is at least 75% of the administered fructose. In other embodiments, the portion is at least 90% of the administered fructose. In other embodiments, the portion is at least 100% of the administered fructose.

Capsule sizes mentioned below refer to the size definitions used by Capsugel Belgium BVBA, Bornem, Belgium. The size of the capsules should be chosen according to the specific formulation of the agent.

An example for the formulation of the agent according to the present invention is the formulation in capsule form with capsules of size 3 containing 75 mg of 5-D-fructose dehydrogenase with an activity of 90 units/mg and 85 mg of dicalcium phosphate.

Another example for the a dosage form according to the present invention consists of capsules of size 1 which contain 150 mg of 5-D-fructose dehydrogenase with an activity of 90 units/mg, 5 mg of folic acid and 150 mg of maltodextrin.

A further dosage form according to the present invention may consists of capsules (size 3) containing 55 mg of 5-D-fructose dehydrogenase with an activity of 500 units/mg, 50 mg of invertase with an activity of 200 SU units/mg and 65 mg of dicalcium phosphate.

A further dosage form according to the present invention consists of capsules (size 3) which contain 55 mg of 5-D-fructose dehydrogenase with an activity of 500 units/mg, as well as 50 mg of maltase with an activity of 200 units/mg and 65 mg of dicalcium phosphate.

A further dosage form according to the present invention consists of capsules (size 1) which contain 110 mg of 5-D-fructose dehydrogenase with an activity of 500 units/mg as well as 100 mg of invertase with an activity of 200 SU units/mg and 90 mg of maltodextrin.

The invention may for example contain between 10 and 5 million units of 5-D-fructose dehydrogenase, between 50 and 250,000 units of invertase, between 100 and 100,000 units of maltase, between 0.01 and 100,000 GIU, between 50 mg and 50 g of glucose and/or between 1 mg and 100 mg of folic acid per dose unit.

Furthermore, suitable additives in useful amounts may be used.

The invention may be provided for medical purposes and non medical purposes, e.g. as a pharmaceutical composition, medical device, foodstuffs or special foodstuffs.

In summary, 5-D-fructose dehydrogenase is suited in an excellent manner for use in the case of fructose intolerance or any disturbance of fructose metabolism. According to preferred embodiments of the invention, 5-D-fructose dehydrogenase optionally in combination with invertase and/or maltase and/or glucose isomerase and/or glucose and/or folic acid are provided as a medicament or are used for the preparation of a medicament for the treatment of fructose intolerance.

Thus, there is provided, in accordance with embodiments of the invention, a 5-D-fructose dehydrogenase, optionally in combination with invertase and/or maltase and/or glucose isomerase, for use in medicine, preferably in the form of a pharmaceutical composition. There is also provided, in accordance with embodiments of the invention, a pharmaceutical composition comprising 5-D-fructose dehydrogenase, optionally in combination with invertase and/or maltase and/or glucose isomerase. In some embodiments, the pharmaceutical composition includes one or more enzyme(s) protected by a coating so as to be stable at pH values of less than 4, preferably less than 3. In some embodiments, the pharmaceutical composition is in a form for oral administration. In some embodiments, the pharmaceutical composition is in a form suited to be added to food at the production stage of the same and/or before eating.

There is also provided, in accordance with embodiments of the invention, a medical device comprising 5-D-fructose dehydrogenase, optionally in combination with invertase and/or maltase and/or glucose isomerase. In some embodiments, the medical device includes one or more enzyme(s) protected by a coating so as to be stable at pH values of less than 4, preferably less than 3. In some embodiments, the medical device is in a form for oral administration. In some embodiments, the medical device is in a form suited to be added to food at the production stage of the same and/or before eating.

There is also provided, in accordance with embodiments of the invention, a foodstuff comprising 5-D-fructose dehydrogenase in combination with invertase and/or maltase. In some embodiments, the foodstuff is a special foodstuff comprising 5-D-fructose dehydrogenase, optionally in combination with invertase and/or maltase and/or glucose isomerase. In some embodiments, the foodstuff includes one or more of the above-mentioned enzymes protected by a coating so as to be stable at pH values of less than 4, preferably less than 3. In some embodiments, the foodstuff is in a form suited to be added to food at the production stage of the same and/or before eating.

There is also provided, in accordance with embodiments of the invention, the use of 5-D-fructose dehydrogenase alone or optionally in combination with invertase and/or maltase and/or glucose isomerase for the production of a product, preferably a pharmaceutical composition, for use in the therapy or diagnosis of disorders of fructose metabolism, including fructose intolerance. There is also provided, in accordance with embodiments of the invention, the use of 5-D-fructose dehydrogenase alone or optionally in combination with invertase and/or maltase and/or glucose isomerase for the production of a product, preferably for the production of a pharmaceutical composition, for lowering the bioavailability of fructose in the human or animal body. There is also provided, in accordance with embodiments of the invention, the use of 5-D-fructose dehydrogenase alone or optionally in combination with invertase and/or maltase and/or glucose isomerase for the production of a product, preferably for the production of a pharmaceutical composition, for lowering the fructose content in foodstuffs. There is also provided, in accordance with embodiments of the invention, the use of 5-D-fructose dehydrogenase alone or optionally in combination with invertase and/or maltase and/or glucose isomerase for the production of a product, preferably for the production of a pharmaceutical composition, for lowering the amount of fructose available to the human or animal body and/or to bacteria of the intestine of the human or animal body. In some embodiments, the product comprises any pharmaceutical composition, a medical device, a foodstuff or a special foodstuff. In some embodiments, the product is coated in such a manner that one or more of the above-mentioned enzymes are protected against pH values of less than 4, preferably less than 3. In some embodiments, the product is in a form for oral use. In some embodiments, the product is suited to be added to food at the production stage of the same and/or before eating. In some embodiments, the product is in a form for use in immobilised form.

There is also provided, in accordance with embodiments of the invention, a process for the treatment of a foodstuff, the process comprising the steps of contacting the foodstuff with a 5-D-fructose dehydrogenase, optionally in combination with invertase and/or maltase, and initiating the reaction of fructose to 5-keto-D-fructose. There is also provided, in accordance with embodiments of the invention, a process for the treatment of a foodstuff, comprising the steps of contacting the foodstuff with a 5-D-fructose dehydrogenase, optionally in combination with invertase and/or maltase and/or glucose isomerase, and initiating the reaction of fructose to 5-keto-D-fructose and optionally the reaction of fructose to glucose. In some embodiments, as a further step prior to the reaction ingestion of the foodstuff takes place.

There is also provided, in accordance with embodiments of the invention, a human-ingestible composition of matter which comprises an enzyme that converts D-fructose into a form that is biologically inactive in the human body or a mixture of such enzymes. There is also provided, in accordance with embodiments of the invention, a human-ingestible composition of matter which comprises an enzyme that converts D-fructose into a form that cannot be digested in the human digestive tract. There is also provided, in accordance with embodiments of the invention, a human-ingestible composition of matter which comprises an enzyme that converts D-fructose into a form that is not metabolizable in the human body. In some embodiments, the form is 5-keto-D-fructose. In some embodiments, the enzyme is 5-D-fructose dehydrogenase. In some embodiments, the composition of matter is a dietary supplement or a pharmaceutical composition. In some embodiments, the composition of matter is a special foodstuff. In some embodiments, the composition of matter further comprises at least one pharmaceutically or dietarily acceptable carrier or excipient. In some embodiments, the composition of matter contains the enzyme in microencapsulated form. In some embodiments, the composition of matter is in the form of a capsule or tablet. In some embodiments, the composition of matter is in the form of granules or pellets. In some embodiments, the composition of matter is in the form of a solution. In some embodiments, the composition of matter is in the form of a gel or suspension. In some embodiments, the composition of matter is in the form of a gelcap.

There is also provided, in accordance with embodiments of the invention, a composition of matter which is microencapsulated 5-D-fructose dehydrogenase. There is also provided, in accordance with embodiments of the invention, a composition of matter comprising 5-D-fructose dehydrogenase admixed with a human-ingestible substance. In some embodiments, the human-ingestible substance is a pharmaceutically or dietarily acceptable carrier or excipient. In some embodiments, the 5-D-fructose dehydrogenase is microencapsulated.

In accordance with some embodiments, the enzyme constitutes between 5 and 99.9% by weight of the composition of matter described above. In some embodiments, the enzyme constitutes between 10 and 80% by weight of the composition of matter. In some embodiments, the enzyme constitutes between 25 and 60% by weight of the composition of matter.

In accordance with some embodiments, the composition of matter as described above is in unit dosage form and the unit dosage contains between 10 and 5 million units of 5-D-fructose dehydrogenase activity. In some embodiments, the unit dosage contains between 25 and 2.5 million units of 5-D-fructose dehydrogenase activity. In some embodiments, the unit dosage contains between 50 and 1 million units of 5-D-fructose dehydrogenase activity.

In accordance with some embodiments, the composition of matter as described above comprises a coating which dissolves in an aqueous medium at a pH of between 3.0 and 8.0. In some embodiments, the coating does not dissolve in an aqueous medium at a pH below 3.0. In some embodiments, the coating does not dissolve in an aqueous medium at a pH below 4.0. In some embodiments, the coating does not dissolve in an aqueous medium at a pH above 6.5. In some embodiments, the coating does not dissolve in an aqueous medium at a pH above 6.0.

In accordance with some embodiments, the composition of matter as described above is a slow-release or extended-release formulation. In some embodiments, the slow-release or extended-release formulation comprises a slow-release or extended-release coating.

In accordance with some embodiments, the composition of matter as described above further comprises a second enzyme. In some embodiments, the second enzyme is capable of cleaving fructose from a more complex sugar. In some embodiments, the second enzyme is invertase or maltase. In some embodiments, the second enzyme is invertase, the composition of matter is in unit dosage form, and each unit dosage contains between 50 and 250,000 Sumner units of invertase activity. In some embodiments, each unit dosage contains between 100 and 150,000 Sumner units of invertase activity. In some embodiments, each unit dosage contains between 150 and 100,000 Sumner units of invertase activity. In some embodiments, the second enzyme is maltase, the composition of matter is in unit dosage form, and each unit dosage contains between 100 and 100,000 units of maltase activity. In some embodiments, each unit dosage contains between 200 and 50,000 units of maltase activity. In some embodiments, each unit dosage contains between 500 and 20,000 units of maltase activity. In some embodiments, the composition of matter comprises both invertase and maltase.

In accordance with some embodiments, the composition of matter as described above further comprises an additional enzyme that converts D-fructose into a molecule that is absorbed more quickly than D-fructose from the intestine into the bloodstream. In some embodiments, the molecule is D-glucose In some embodiments, the additional enzyme is a glucose isomerase. In some embodiments, the composition of matter is in unit dosage form and each dosage unit contains 0.01 to 100,000 units of glucose isomerase activity per dosage unit. In some embodiments, each dosage unit contains 0.05 to 10,000 units of glucose isomerase activity per dose unit. In some embodiments, each dosage unit contains 0.1 to 1,000 units of glucose isomerase activity per dose unit. In some embodiments, the glucose isomerase is a xylose isomerase. In some embodiments, the composition of matter further comprises at least one of an electrolyte and a metal ion. In some embodiments, the electrolyte is selected from the group consisting of $MgSO_4$, $Na_2CO_3$, $NaHCO_3$, $NaOH$, $Na_2SO_4$, $MgCO_3$, $H_2SO_4$, $NaS_2O_3$, $NaS_2O_5$ and mixtures of any of these compounds. In some embodiments, the metal ion is selected from the group consisting of $Mn^{2+}$, $Mg^{2+}$, $Ca^{2+}$, $Zn^{2+}$, $Fe^{2+}$, $Co^{2+}$, $Cu^{2+}$ and mixtures of any of these compounds.

In accordance with some embodiments, the composition of matter as described above is in unit dosage form, and each dosage unit further comprises from 50 to 50,000 mg of glucose. In some embodiments, each dosage unit comprises from 500 to 25,000 mg of glucose. In some embodiments, each dosage unit comprises from 1,000 to 15,000 mg of glucose.

In accordance with some embodiments, the composition of matter as described above is in unit dosage form, and each dosage unit further comprises from 1 to 100 mg of folic acid. In some embodiments, each dosage unit comprises from 2 to 50 mg of folic acid. In some embodiments, each dosage unit comprises from 3 to 10 mg of folic acid.

In accordance with some embodiments, the composition of matter as described above is a foodstuff, and the enzyme is in active form. In some embodiments, the amount or concentration of the enzyme in the foodstuff is greater than the naturally occurring concentration or amount of the enzyme in the foodstuff. In some embodiments, the foodstuff is a fructose-containing foodstuff. In some embodiments, the foodstuff is a foodstuff which has been baked. In some embodiments, the foodstuff is a foodstuff which has been cooked. In some embodiments, the foodstuff is a liquid, paste or broth. In some embodiments, the enzyme is present in microencapsulated form. In some embodiments, the enzyme is 5-D-fructose dehydrogenase. In some embodiments, the foodstuff further contains a second enzyme in active form. In some embodiments, the concentration or amount of the second enzyme in the foodstuff is greater than the naturally occurring concentration or amount of the second enzyme in the foodstuff. In some embodiments, the second enzyme is invertase. In some embodiments, the second enzyme is maltase. In some embodiments, the second enzyme is a glucose isomerase. In some embodiments, the glucose isomerase is a xylose isomerase. In some embodiments, the composition further comprises at least one of an electrolyte and a metal ion. In some embodiments, the electrolyte is selected from the group consisting of $MnSO_4$, $Na_2CO_3$, $NaHCO_3$, $NaOH$, $Na_2SO_4$, $MgCO_3$, $H_2SO_4$, $NaS_2O_3$, $NaS_2O_5$ and mixtures thereof. In some embodiments, the metal ion is selected from the group consisting of $Mn^{2+}$, $Mg^{2+}$, $Ca^{2+}$, $Zn^{2+}$, $Fe^{2+}$, $CO^{2+}$, $Cu^{2+}$ and mixtures thereof. In some embodiments, the second enzyme is a mixture of at least two of the group of invertase, maltase and a glucose isomerase. In some embodiments, the second enzyme is in microencapsulated form.

In accordance with some embodiments, the composition of matter as described above comprises a mixture of enzymes that convert D-fructose into a form that is at least one of (a) biologically inactive in the human body, (b) not digestible in the human digestive tract and (c) not metabolizable in the human body.

In accordance with some embodiments, the foodstuff described above is not a dough.

In accordance with some embodiments, the enzyme that converts D-fructose into a form that is at least one of (a) biologically inactive in the human body, (b) not digestible in the human digestive tract and (c) not metabolizable in the human body is not contained in an inorganic-based sol-gel biocompatible matrix.

In accordance with some embodiments, the composition is substantially free of substances which are not approved for oral human ingestion.

In accordance with some embodiments, the composition of matter is adapted for oral ingestion.

In accordance with some embodiments, the composition comprises an electron acceptor. In some embodiments, the electron acceptor is selected from the group consisting of Nicotinamide Adenine Dinucleotide+(NAD+), nicotinamide adenine dinucleotide phosphate+(NADP+), flavin adenine dinucleotide+, vitamin C, E or A, ferricyanide, ketones, aldehydes, 2,6-di-chloro-phenolindophenol, phenazine methosulfate and mixtures thereof. In some embodiments, the molar ratio of electron acceptor to fructose is from 1:1 to 1:1000. In some embodiments, the molar ratio of electron acceptor to fructose is from 1:2 to 1:200. In some embodiments, the molar ratio of electron acceptor to fructose is from 1:10 to 1:50.

There is also provided, in accordance with embodiments of the invention, a method of treating fructose intolerance or impaired fructose metabolism, comprising administering to a human or animal subject an efficacious amount of an enzyme or a mixture of enzymes that converts D-fructose into a form that is at least one of (a) biologically inactive in the subject body, (b) not digestible in the subject digestive tract and (c) not metabolizable in the subject body. In some embodiments, the subject is a human subject. In some embodiments, the administering comprises administering a human-ingestible composition of matter as described above. In some embodiments, the fructose intolerance is hereditary fructose intolerance. In some embodiments, the fructose intolerance is intestinal fructose intolerance. In some embodiments, the fructose intolerance is due to a lack of fructose 1,6-diphosphatase. In some embodiments, the composition of matter is administered immediately prior to eating. In some embodiments, the composition of matter is administered concurrently with a meal. In some embodiments, the composition of matter is administered immediately after eating. In some embodiments, the form is 5-keto-D-fructose.

There is also provided, in accordance with embodiments of the invention, a method for diagnosing fructose intolerance, comprising administering to a human or animal subject exhibiting the symptoms of fructose intolerance a composition of matter as described above and observing if the administering partly or fully ameliorates said symptoms. In some embodiments, the subject is a human subject.

There is also provided, in accordance with embodiments of the invention, a method for diagnosing fructose intolerance, comprising administering to a human or animal subject known to exhibit the symptoms of fructose intolerance both (a) an amount of fructose effective to induce such symptoms and (b) a composition of matter as described above which comprises an enzyme that converts fructose, or mixture of such enzymes, in an amount which is sufficient to convert at least 50% of the amount of fructose, and assessing the results of the administration of the enzyme or mixture thereof. In some embodiments, the composition comprises the enzyme that converts fructose, or mixture of such enzymes, in an amount which is sufficient to convert at least 75% of the amount of fructose. In some embodiments, the composition comprises the enzyme that converts fructose, or mixture of such enzymes, in an amount which is sufficient to convert at least 90% of the amount of fructose. In some embodiments, the composition comprises the enzyme that converts fructose, or mixture of such enzymes, in an amount which is sufficient to convert substantially all of the amount of fructose. In some embodiments, the enzyme or mixture of enzymes converts D-fructose to 5-keto-D-fructose. In some embodiments, the subject is a human subject.

There is also provided, in accordance with embodiments of the invention, a kit comprising an enzyme that converts D-fructose into a form that is at least one of (a) biologically inactive in the human body, (b) not digestible in the human digestive tract and (c) not metabolizable in the human body, or a mixture of such enzymes, and instructions explaining how to use the enzyme or mixture thereof to diagnose or treat fructose intolerance. In some embodiments, the enzyme or mixture thereof is present as a composition of matter as described above. In some embodiments, the enzyme or mixture of enzymes converts D-fructose into 5-keto-D-fructose.

There is also provided, in accordance with embodiments of the invention, a reduced-fructose foodstuff.

There is also provided, in accordance with embodiments of the invention, a method for preparing a reduced-fructose foodstuff, comprising contacting a foodstuff or foodstuff precursor with an enzyme that converts D-fructose into a form that is at least one of (a) biologically inactive in the human body, (b) not digestible in the human digestive tract and (c) not metabolizable in the human body, and completing any additional steps necessary to prepare the foodstuff. In some embodiments, the enzyme is 5-D-fructose dehydrogenase. In some embodiments, the foodstuff is not a baked foodstuff. In some embodiments, the foodstuff is not bread. In some embodiments, the foodstuff is not a dough. In some embodiments, the enzyme converts D-fructose to 5-keto-D-fructose.

The invention claimed is:

1. A mammalian ingestible composition of matter which is adapted for oral administration selected from a pharmaceutical composition and a dietary supplement, said composition of matter being in unit dosage form, said composition of matter comprising isolated, dry, active 5-D-fructose dehydrogenase and a carrier or excipient that is acceptable for use in pharmaceutical compositions or foodstuffs, wherein said 5-D-fructose dehydrogenase is not contained in an inorganic-based sol-gel biocompatible matrix, said 5-D-fructose dehydrogenase constitutes between 25 and 80% by weight of the composition of matter, and the unit dosage form is a tablet.

2. A composition of matter according to claim 1, further comprising a second enzyme which is selected from the group consisting of invertase, maltase and combinations thereof.

3. A mammalian ingestible composition of matter according to claim 1 wherein the composition of matter is a dietary supplement.

4. A mammalian ingestible composition of matter according to claim 1 wherein said unit dosage form contains between 10 and 5 million units of 5-D-fructose dehydrogenase activity.

5. A mammalian ingestible composition of matter according to claim 4 wherein said unit dosage form contains between 50 and 1 million units of 5-D-fructose dehydrogenase activity.

6. A composition of matter according to claim 1 wherein said 5-D-fructose dehydrogenase is protected by a coating which is stable at pH below 4.

7. A composition of matter according to claim 6 wherein said composition of matter is in unit dosage form and said coating protects the entire dosage unit.

8. A composition of matter according to claim 1 wherein said composition of matter comprises a coating which dissolves at a pH of 5.5 or higher.

9. A composition of matter according to claim 1 wherein said 5-D-fructose dehydrogenase is not contained in an inorganic-based sol-gel biocompatible matrix.

10. A composition of matter according to claims 1 wherein said composition of matter comprises a coating which dissolves in an aqueous medium at a pH of between 3.0 and 8.0.

11. A composition of matter according to claim 10 wherein said coating does not dissolve in an aqueous medium at a pH of below 3.0.

12. A composition of matter according to claim 10 wherein said coating does not dissolve in an aqueous medium at a pH below 4.0.

13. A composition of matter according to claims 10 wherein said coating does not dissolve in an aqueous medium at a pH above 6.5.

14. A composition of matter according to claim 10 wherein said coating does not dissolve in an aqueous medium at a pH above 6.0.

15. A composition of matter according to claim 1 wherein said composition of matter is a slow-release or extended-release formulation.

16. A composition of matter according to claim 15 wherein said slow-release or extended-release formulation comprises a slow-release or extended-release coating.

* * * * *